(12) United States Patent
Doyle et al.

(10) Patent No.: US 6,194,890 B1
(45) Date of Patent: Feb. 27, 2001

(54) METHOD AND APPARATUS FOR MONITORING PHYSICAL INTEGRITY OF A WALL IN A VESSEL

(75) Inventors: Patrick J. Doyle, Plymouth; David L. Van Olinda, Westborough, both of MA (US)

(73) Assignee: Quantum Catalytics, L.L.C., Fall River, MA (US)

( * ) Notice: Subject to any disclaimer, the term of this patent is extended or adjusted under 35 U.S.C. 154(b) by 0 days.

(21) Appl. No.: 09/336,243

(22) Filed: Jun. 18, 1999

Related U.S. Application Data

(63) Continuation of application No. PCT/US97/23118, filed on Dec. 16, 1997
(60) Provisional application No. 60/033,711, filed on Dec. 20, 1996.

(51) Int. Cl.[7] ............................... G01N 27/20; H05B 6/06
(52) U.S. Cl. ..................... 324/71.2; 324/71.1; 137/145
(58) Field of Search ..................... 324/240, 228, 324/551, 557, 691, 713, 71.1, 71.2; 137/145; 340/640, 605

(56) References Cited

U.S. PATENT DOCUMENTS

| | | | |
|---|---|---|---|
| 1,922,029 | * 8/1933 | Chesnut | 137/145 |
| 4,574,714 | 3/1986 | Bach et al. | 110/346 |
| 4,584,521 | 4/1986 | Gaud et al. | 324/54 |
| 4,602,574 | 7/1986 | Bach et al. | 110/346 |
| 5,612,622 | 3/1997 | Goldman et al. | 324/444 |

FOREIGN PATENT DOCUMENTS

| | | |
|---|---|---|
| 3220804 A1 | 4/1983 | (DE) . |
| 0 077 757 A1 | 10/1982 | (EP) . |
| 0 721 103 A1 | 7/1996 | (EP) . |

* cited by examiner

Primary Examiner—Walter E. Snow
(74) Attorney, Agent, or Firm—Hamilton, Brook, Smith & Reynolds, P.C.

(57) ABSTRACT

An apparatus and method is described for monitoring the physical integrity of a vessel, such as a molten metal reactor. The apparatus includes a vessel for containing an electrically-conductive liquid having at least one electrically-grounded detection unit located within the containment wall of the vessel. Monitoring changes in electrical current flow of the detection unit relates to the physical integrity of the vessel containment wall and prevents unanticipated breaching of the vessel by the electrically-conductive liquid.

20 Claims, 4 Drawing Sheets

METHOD AND APPARATUS FOR MONITORING PHYSICAL INTEGRITY OF A WALL IN A VESSEL

RELATED APPLICATIONS

This application is a continuation of international application no. PCT/US97/23118, filed on Dec. 16, 1997, which claims priority to U.S. provisional application Ser. No. 60/033,711, filed on Dec. 20, 1996, the entire teachings of which are incorporated herein by reference.

BACKGROUND OF THE INVENTION

Processing of many types of industrial materials, including treatment by molten bath reactors of industrial wastes composed of, for example, organic compositions, such as polychlorinated biphenyls, metals and their oxides, etc., is often conducted in a heated containment vessel. In molten bath reactor systems, the containment vessel is constructed of a material, usually a refractory material, which will not fail while retaining the heated molten material. Repeated use of containment vessels and the stresses of heating and cooling molten baths can cause containment vessels to fail unexpectedly and catastrophically. Catastrophic failure of a refractory lining in a vessel can cause serious bodily injury and can result in loss of life as well as significant property damage.

Currently, a method to determine failure of a vessel wall lining is by visual inspection. However, inspection by this method involves discontinuing the process and removing any materials contained within the vessel for inspection of the lining. Consequently, an indication of catastrophic failure while the reactor is filled with a liquid, such as molten metal, generally cannot be determined until the failure occurs.

A need exists, therefore, for an apparatus and a method to monitor the physical integrity of containment vessels such as the type which retain heated molten materials.

SUMMARY OF THE INVENTION

The present invention relates to a method and apparatus for monitoring the physical integrity of a wall of a vessel, for example, the refractory wall of a molten bath reactor.

The apparatus includes a vessel for containing an electrically-grounded, electrically-conductive liquid and at least one electrically-grounded detection unit located within the containment wall of the vessel. An alternating magnetic field is established so as to impose a voltage on the detection unit. A means for measuring current flow is provided between the electrically-grounded, electrically-conductive liquid contained within the vessel and the detection unit to sense whether the liquid has contacted the detection unit, whereby the physical integrity of the wall can be monitored.

The method includes establishing an alternating magnetic field to impose a voltage on a detection unit contained within the wail of a vessel containing an electrically-grounded, electrically-conductive liquid. The method also includes measuring current flow between the liquid contained within the vessel and the detection unit to sense whether the liquid has contacted the detection unit.

This invention has the advantage, for example, of detecting the loss of physical integrity of a containment wall of a vessel prior to the time a breach of the wall of the vessel by a liquid occurs. In addition, the invention has the advantage of not requiring the removal of material within the vessel to inspect the containment lining.

DETAILED DESCRIPTION OF THE INVENTION

The features and other details of the apparatus and method of the invention will now be more particularly described with reference to the accompanying drawings and pointed out in the claims. It will be understood that the particular embodiments of the invention are shown by way of illustration and not as limitations of the invention. The principle features of this invention can be employed in various embodiments without departing from the scope of the invention.

The present invention relates generally to an apparatus and a method for monitoring the physical integrity of a wail of a vessel, for example, the refractory wail of a molten bath reactor, by measuring the current flow between an electrically-conductive liquid within the vessel and at least one detection unit located within the containment wall of the vessel. A process and apparatus for dissociating waste in molten baths are disclosed in U.S. Pat. Nos. 4,574,714 and 4,602,574 whose disclosures are hereby incorporated by reference.

Figure 1:
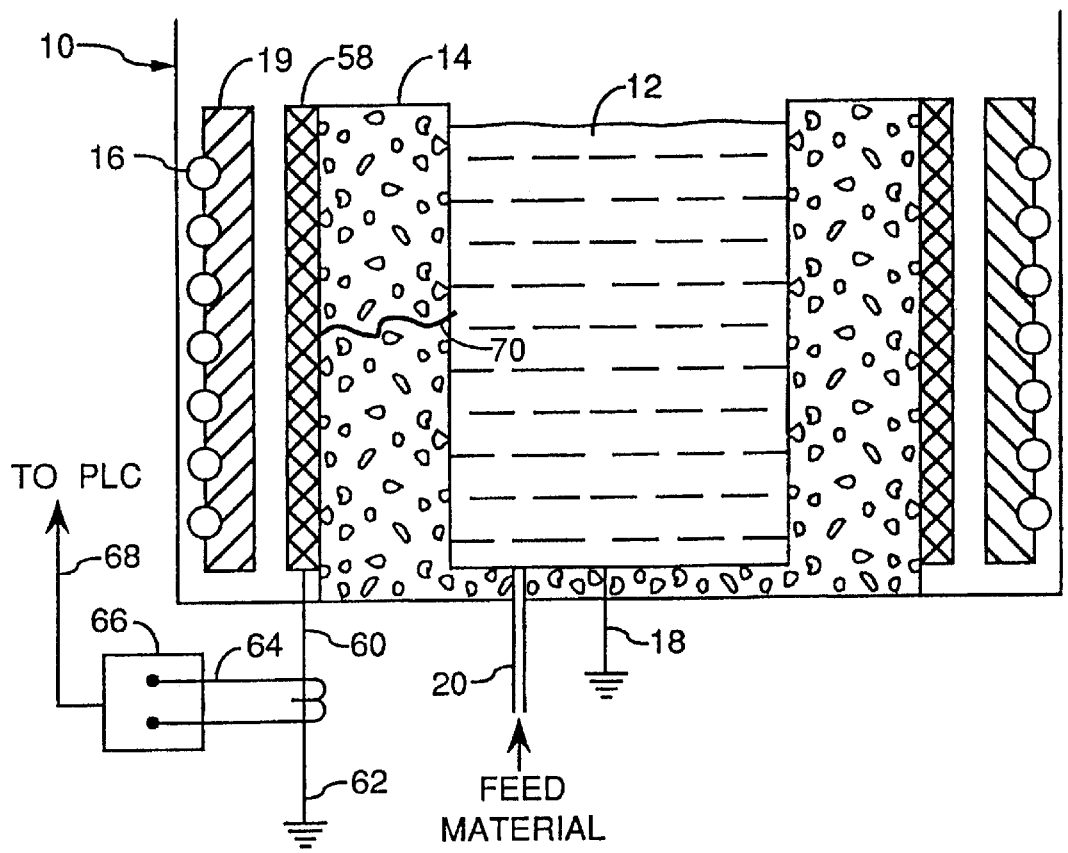
FIG. 1 is a schematic representation, set forth partly in cross section, of one embodiment of the apparatus of the invention.

One embodiment of the apparatus of the invention is illustrated in FIG. 1. The apparatus includes vessel 10 for containing molten bath 12 such as may be suitable for dissociating waste. Vessel 10 includes refractory wall 14 which surrounds and contains molten bath 12. Induction coil 16 surrounds outer portion of refractory wall 14 of vessel 10. Grid 58 is positioned between the outer portion of refractory wall 14 and induction coil 16.

Vessel 10 contains electrically-conductive molten bath 12 and is electrically-grounded through grounding means 18. Electrically-conductive bath 12 includes at least one electrically-conductive liquid so that bath 12 is, itself, electrically-conductive. Grounding means 18 can be, for example, a copper wire.

"Electrically-conductive material," as that term is used herein, means a substance or substances which are or become electrically-conductive in a liquid state. Examples of electrically-conductive materials include aqueous solutions, particulate metals, molten metals, molten metal oxides, molten salts, molten mattes and combinations thereof. Examples of suitable components of electrically-conductive bath 12 include copper, tin, iron, nickel, etc. Conditions suitable for electrical conduction, for example, include exposure of a metal to a temperature suitable for melting the metal. In particular, electrically-conductive bath 12 can be a molten bath. In one embodiment, the composition of electrically-conductive bath 12 is suitable for dissolving at least a portion of a waste feed material directed into electrically-conductive bath 12 by means of tuyere 20 which is located in the bottom of refractory wall 14.

Electrically-conductive bath 12 can include more than one metal component. For example, electrically-conductive bath 12 can include a solution of molten metals, such as a solution of copper and nickel. Suitable examples of molten metal can include actinide and transition metals. Additionally, electricaly-conductive bath 12 can include metal alloys. Alternatively, electrically-conductive bath 12 can include at least two immiscible molten metals. In one embodiment, where electrically-conductive bath 12 is formed, for example, of iron or nickel, the temperature of the bath is typically in a range of between about 1,300° C. and 1,700° C.

Induction coil 16 is located within vessel 10, but electrically isolated from vessel 10, bath 12 and grid 58, and extends about refractory wall 14. Induction coil 16, which is suitable for heating or maintaining the temperature of the contents of molten bath 12, is encased with a high temperature grout to form insulating liner 19. As will be explained in detail below, a secondary aspect of the induction coil operation is to impose a voltage on grid 58 to allow measurement of current flow as may occur if electrically-conductive molten bath 12 contacts grid 58, thereby monitoring the physical integrity of refractory wall 14 of vessel 10.

As shown in FIG. 1, grid 58 is positioned between liner 19 and refractory wall 14. Induction coil 16, when energized, induces electromagnetic flux lines on grid 58. The flux lines induce a voltage on grid 58 by transformer action. Lead wire 60 is attached to grid 58 at one end and to electrical ground 62 at second end. Current flow through lead wire 60 can be detected by current sensor 64 which is a wire wound around lead wire 60. Current sensor 64 is connected to current transducer 66 for converting the sensed current flow to an analog value, such as 4–20 milliampere (ma). This analog signal is fed to programmable logic controller (PLC) (not shown) through wire 68. PLC converts the sensed current to a readily usable digital signal level, Under normal operating conditions, essentially no current flows from grid 58 through lead wire 60 because there is no return path to grid 58. If refractory wall 14 develops a crack 70 or erodes sufficiently, such that molten bath 12 can contact grid 58, an electrical current path from molten bath 12 through crack 70 to grid 58 is established. The voltage induced on grid 58 from the influence of the alternating magnetic field imposed by induction coil 16 causes current to flow through lead wire 60 to ground 62 to molten bath 12 through molten bath ground 18 and then to return to grid 58 through crack 70.

Figure 2A:
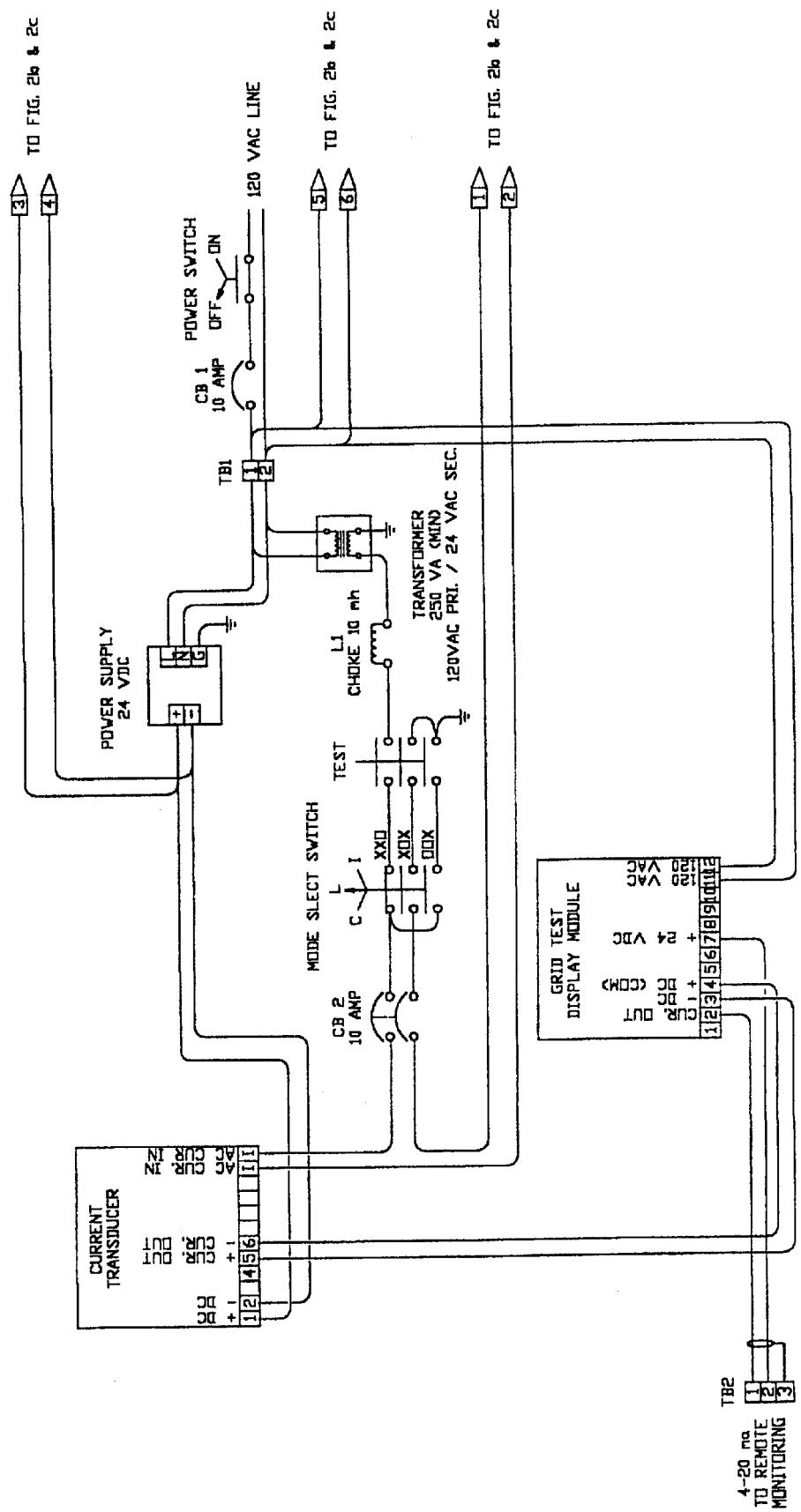
FIGS. 2A, 2B and 2C are a schematic diagram of the electronic circuitry for a dual grid detection unit in accordance with an embodiment of the apparatus of the invention.
Figure 2B:
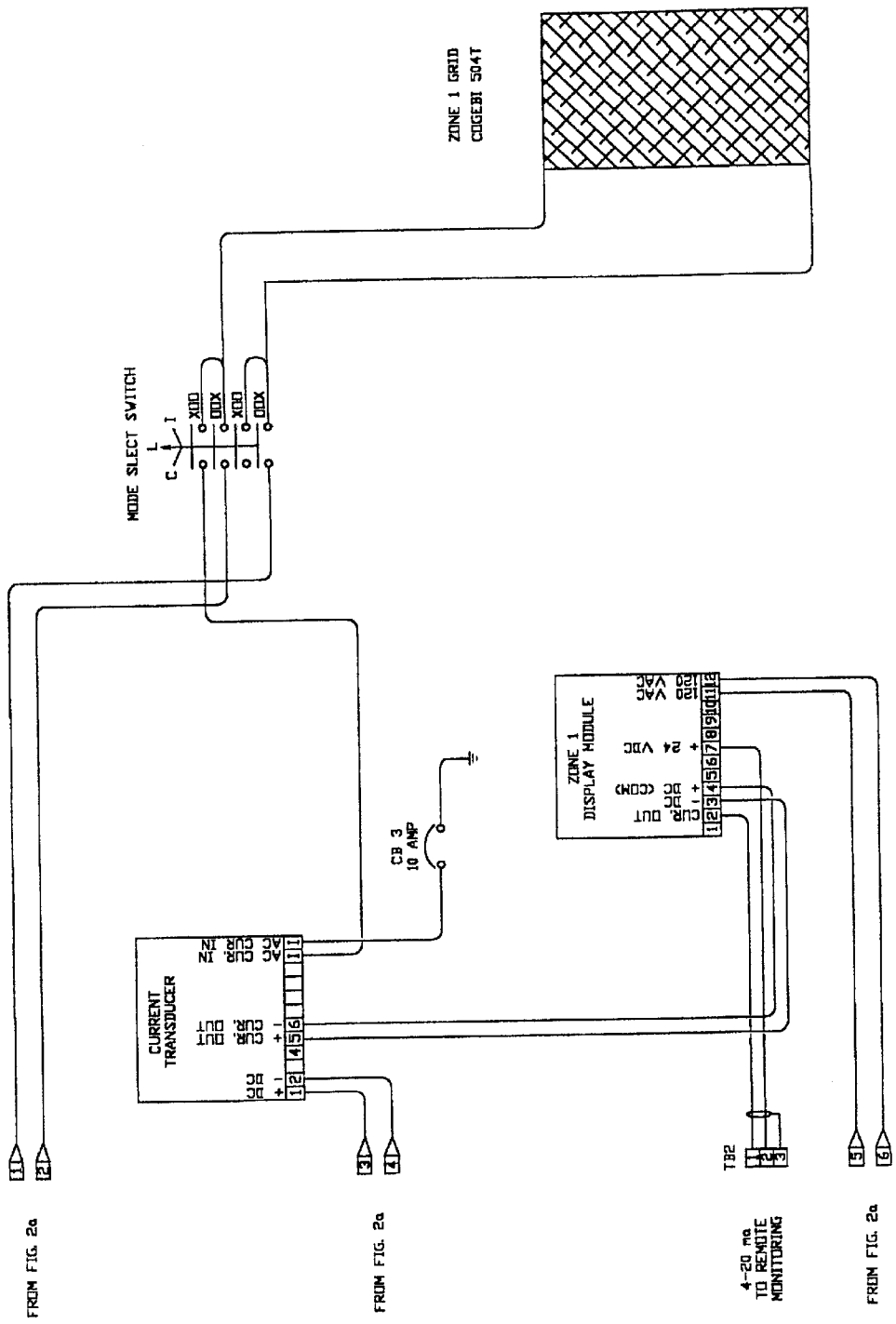
Figure 2C:
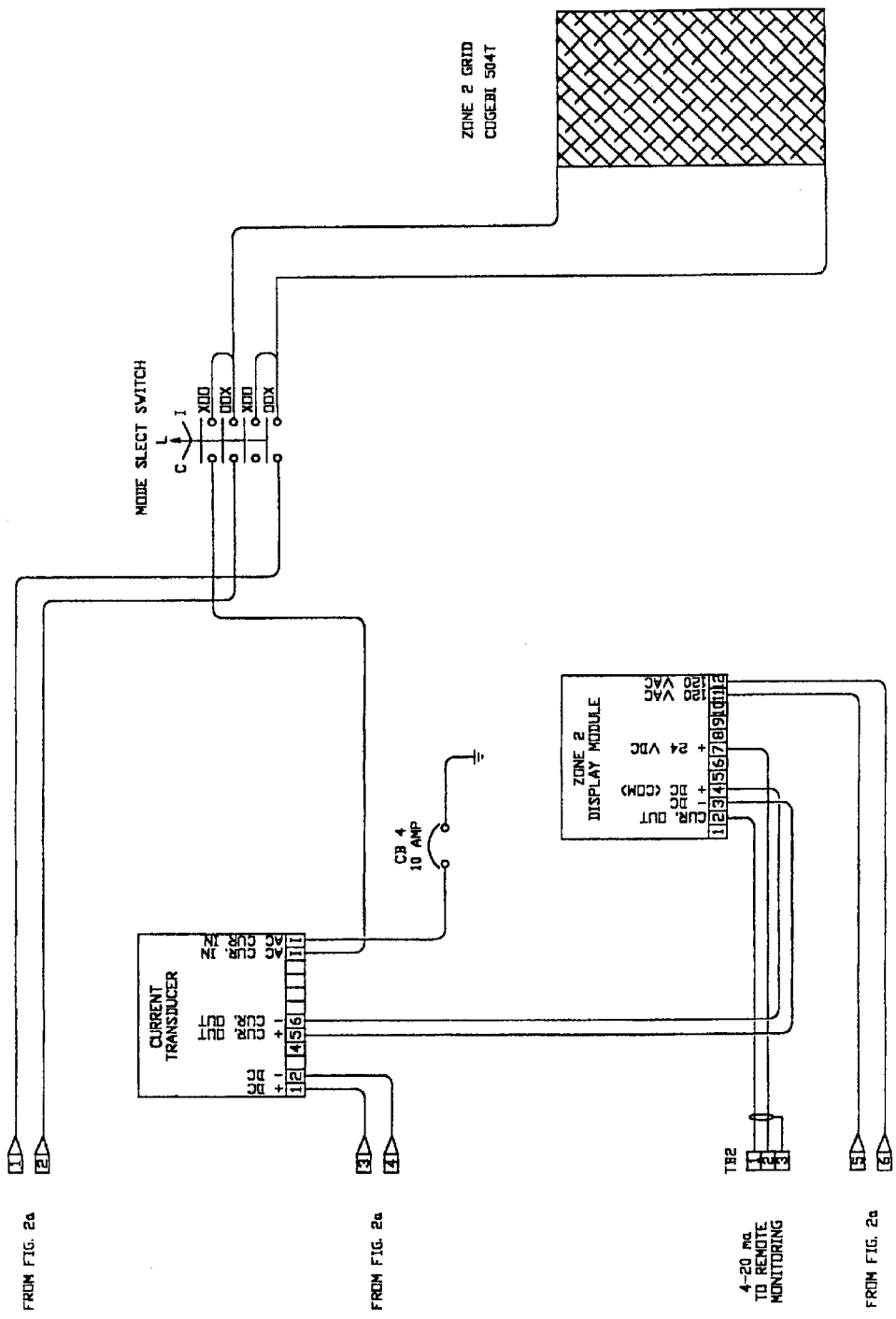

Grid 58 includes a latticed metal material (available from Cogebi Inc. 504T) comprised of a 316 stainless steel mesh substrate embossed by two sheets of 10 millimeter thick mica. In one embodiment, the mesh is formed of 0.2 millimeter diameter stainless steel wire. The wires are spaced 1.6 millimeters apart. Grid 58 is installed adjacent liner 19 along essentially the entire periphery of induction coil 16. Grid 58 is then interfaced to current sensor 64 and current transducer 66 by means of 16 gauge copper cables. The reactor system can include a single grid with its associated current sensor/transducer circuitry. For particularly large reactor systems, a plurality of grids can be positioned strategically around the vessel, as long as each of the plurality of grids remain under the influence of the alternating magnetic field generated by induction coil 16. The electronic circuitry for a multi-grid system includes individual current transducers, a process monitor, a test transformer, circuit breakers, a current limiting choke and various selector switches to provide isolation of individual grids and for selection of the various test modes described below. FIGS. 2A, 2B and 2C are a schematic diagram of a two zone (Zone 1 and Zone 2) detection unit. Although only two grids are employed in the FIGS. 2A, 2B and 2C embodiment, the principles can be extended to a multiplicity of grids which can be useful to further isolate the located of failures within the reactor system. Analog outputs in the form of 4–20 ma signals are available to be sent to a PLC or distributed control system (DCS) for trending, remote monitoring and diagnostic functioning. Though such 4–20 ma signals are available they need not be connected as the electronic monitoring system is designed for "stand alone" service. The system can be housed in a National Electrical Manufacturers Association (NEMA) Type 4 enclosure, which is watertight and dusttight and can be provided with a clear polycarbonate access door which allows for unobstructed viewing of the current monitors as well as easy access of all mode and test switches by process operators.

As mentioned, the grids must reside in those sections of vessel 10 where they can be exposed to an alternating magnetic field produced by induction colt 16. This causes the grids to be mutually coupled to induction coil 16 via transformer action. An analogy can be drawn using a standard transformer. Induction coil 16 can be compared to the primary of a transformer and the grids can be compared to the secondary. When power is applied to the induction coil, magnetic lines of force emanating from the induction coil cut across the grids inducing a voltage on the grid. This can then be compared to the voltage that is produced on the secondary of transformer when power is applied to the primary. The amount of the voltage produced in the secondary of the transformer is a product of the turns ratio between the primary and the secondary. For example, If 100 turns of wire are in the primary winding and 10 turns of wire are in the secondary winding, and then if 100 volts is applied to the primary winding, the secondary voltage would be $\frac{1}{10}$th of the primary, or 10 volts. The same principle holds between induction coil 16 and grid 58. For example, If the induction coil is made of ten turns and the grid has one turn, If a voltage of 100 volts is applied to induction coil 16, then $\frac{1}{10}$th of that voltage (i.e. 10 volts) would be induced on grid 58.

If lead wire 60 is connected to one corner of grid 58 and then the other end of the wire is connected to ground via current sensor 64, half of the current loop is closed, but no current will flow absent a completion of the electrical circuit. This is similar to taking the secondary of the transformer analogy and grounding one side. No current would flow to ground, because the other side the secondary is not connected anywhere. Now, if a metal finger from electrically-conductive molten bath 12 contained in vessel 10 migrates towards grid 58 through crack 70 in refractory wall 14 and comes in contact with grid 58, and assuming the bath is grounded either by grounding means 18 or tuyere 20 or electrodes (not shown) cast in the bottom refractory wall 14 of vessel 10, a complete circuit is made causing current to flow. If the other side of the transformer secondary is also grounded, a current flow forms a closed loop from one side of the secondary to ground back up the other side to the secondary. Similarly, the grid current flows from one side of the grid through the metal finger, through the molten bath 12 to ground back to grid 58 via the connected 16 gauge wire to form a closed loop. It is this "induced current" that is measured and then converted to a 4–20 ma analog signal for use by the local current indicators and the PLC/DCS.

Once current flows as a result of contact between molten bath 12 and grid 58, current transducer 64 detects the amount of current and converts it to a linear 4–20 ma signal. The 4–20 ma signal is fed to a local "process monitor" display, which can be located in the NEMA Type 4 enclosure. The display can convert the 4–20 ma signal to a 0–10 amp value representative of the true current flowing between grid 58 and molten bath 12.

The display also can repeat the 4–20 ma signal from the "current transducer" and can send it to the PLC for remote monitoring, trending, alarm set points, etc. Circuits carrying critical currents are protected by 10 amp circuit breakers also located in the NEMA Type 4 enclosure.

The electronics system of the present invention can include an on board test circuit for checking grids for shorts to ground (other than the designed short through the 16 gauge wire) or wires that may not be physically connected to the grids as a result of corrosion or accidental breaking during containment installation. The monitoring system can also provide a status of newly installed grids to determine whether the circuit is properly configured. The test circuit can also provide an alternate means of exciting the grids with the on board transformer by injecting a stable 24 volts alternating current 5 amp signal onto the grids. This feature provides an independent means to check for metal contact between molten bath 12 and grid 58 without having to power induction coil 16. The test circuit can also check the electronics system components for proper operation. Three position selector switches allow for optimal identification of "suspect grids". The switches determine if the grids are connected to the, "monitoring circuit" (normal position) or the "test circuit" (test position), or "isolated" (off position) from the system altogether. This can be very helpful in multi-grid systems when trying to identify which grid is providing a fault indication, as this methodology allows for "process of elimination" techniques. Test modes available for monitoring, which are to be used in conjunction with the selector switches, are (1) "Induced", which should be the normal mode for monitoring; (2) "leakage", which checks for shorts of the grids to ground (other than the designed short); and (3) "continuity", which checks the integrity of the wire connections to the grids.

The test circuit incorporates a 120 volt alternating current/24 volt alternating current 60 Hz step down transformer used to excite the grids independent of induction coil 16. One side of the transformer is grounded while the other side is connected in series with a 10 millihenries choke to limit test current to about 5–6 amps, a test push-button to activate the test, a mode selector switch to determine the type of test, a 10 amp circuit breaker to protect the wiring, a current transducer to measure the test current and a process monitor to display the results.

The "induced" test mode allows for checking the coupling of a grid to the induction coil to determine whether the grid is functional and able to provide a usable signal if it were to come in contact with the molten bath. For example, assuming power to the induction coil is on, to determine if grid 1 in zone 5 is healthy, the "test mode" selector switch, is set to "induced". On the "zone 1, grid 1" selector switch, select the "test" position. The "test" push-button is pressed and held and the result on the "grid test" process display is read. The value should increase from zero to a higher value. The amount of the value is not important, as this will be a product of many variables most importantly the induction coil wattage and frequency. Another test to confirm that coupling exists is to perform the aforementioned test while increasing and decreasing the induction coil power. If the values shown on the "grid test" process display track the increase and decrease of the induction coil power, then good coupling exists.

The "leakage" test mode allows for checking grid isolation from ground. A low resistance path to ground from the grid results in a current flow to ground when induction coil power is turned on. This mode should be used when new grids are installed to help determine if there are any installation errors. It should also be used as an independent means to check whether a grid has been contacted or not by the molten bath. For example, if during normal operation the current value reported for any zone increases to a new value, it can be assumed that a grid was contacted by the molten bath through a crack in the refractory wail. The power to the vessel coil can be shut down to observe what happens to the displayed value (it should go to zero). The next step is to select the "leakage test" mode and inject the 24 volt alternating current signal from the onboard transformer, record the reading on the "grid test" process display and then using Ohm's law determine the field resistance. For example, to test for shorts after a new grid installation or if a grid is suspected of being "hit" by the "melt", the induction coil power is shut down, and "leakage" on the "test mode" selector switch is selected. The "test" push-button is pressed and held, and the value on the "grid test" process display is read. A normal condition should show a value of zero amps, an abnormal value is any value greater than zero with a value of as high as about 6 amps.

The "continuity" test mode allows for checking the integrity of the connection of the 16 gauge lead wires to the grids as well as any other components. The 24 volt alternating current from the board transformer is directed to the grid selected. The signal is sent to the grid on one wire and returned to the transformer on the other. The results are then displayed on the "grid test" process display as a value that should equal about 5 amps. For example, to check the continuity of grid 3 in zone 2, select "continuity" on the test mode selector, then on the "zone 2, grid 3" selector switch select "test". The "test" push-button is pressed and held, and the value on the "grid test" process display is read.

In the "normal" mode, all "zone/grid" selector switches are set to the "norm" position. With the switches in this position, all grids in a zone are connected in parallel to a zone current transducer and process monitor. In one embodiment, five zones and five grids per zone form a system. With power to the induction coil on, and in the event that a "metal finger" from the molten bath should come in contact with a grid, this condition will cause an increase in current that is shown on the zone process monitor to which it is connected. Then, by a process of elimination an operator can identify which grid in the zone is not working. Sequentially turning the "norm/off/test" switch for each grid in a zone to the "off" position until the current shown on the zone process monitor drops to zero, identifies the suspect grid. Once a grid has been identified as a problem in the "normal" mode, further diagnosis can be carried out using one of the test functions provided as part of the test circuit. In the normal position, the grids are isolated from the test circuit so that regardless of what test function is selected no test can be imposed on the grids.

Figure 3:
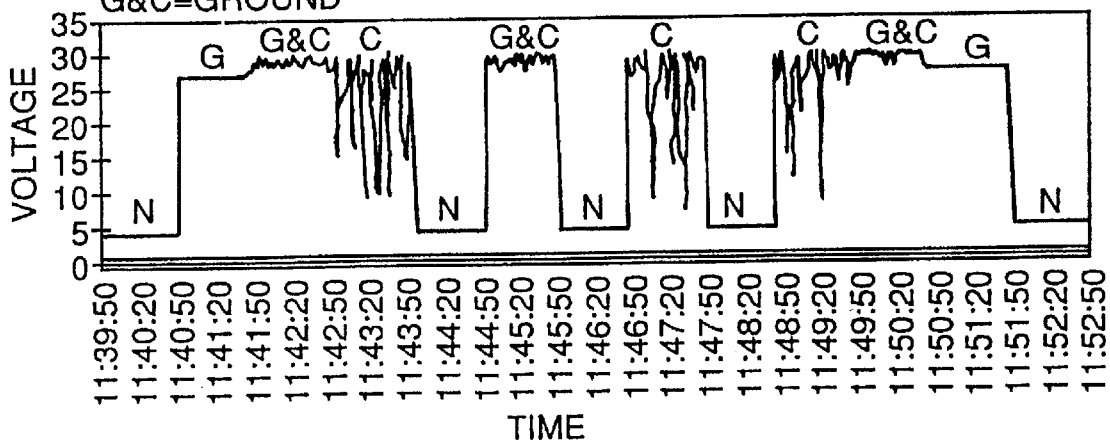
FIG. 3 is a graph of the response of the current sensing apparatus of the embodiment of FIG. 1 showing the differentiation of false positive conditions from actual failures.

In accordance with an important aspect of the present invention, as for example when the molten bath forms a reaction zone for the processing of waste, it is possible during system operation to differentiate between conditions where grid 58 has inadvertently become connected to a ground ("false positive" condition) and where molten bath 12 has actually penetrated refractory wail 14 and contacted grid 58 ("failure mode" condition). FIG. 3 depicts the sample response of the system to the four possible conditions that may occur during operation. These are as follows:

"N"—Normal

The normal response as would be the case when grid 58 Is not in contact with a grounded object.

"G"—Grounded

The condition of grid 58 touching any grounded object other than molten bath 12 (a false positive)

"G & C"—Ground and Charge

The condition wherein grid 58 is in contact both with a grounded object (false positive) and also with molten bath 12.

"C"—Charge

The condition wherein grid 58 is in contact with molten bath 12 only.

Example/Test Setup

A grid was imbedded in the refractory wall of a molten metal bath reactor in the manner described above. The two lead wires normally connected to the grid were brought out of the reactor to a junction box. A stainless steel probe was inserted below the melt line of the metal bath perpendicular to the induction coil wall. A wire was attached to the probe and also was brought to the junction box. The purpose of the probe was to simulate metal contact with the grid (a "finger") by connecting the probe to the grid. Submerged injection of feed material was commenced through a tuyere located in the bottom of the refractory wail. With switch 1 and switch 2 open (simulating a normal state) there is no current flow from the grid to ground and back again, therefore the responses labeled "N" in FIG. 3 are applicable.

When switch 1 is closed, simulating a grid contacting ground or (false positive), the responses labeled "G" in FIG. 3 are applicable.

When switch 2 is closed, simulating a "finger" contact with the molten bath, the responses labeled "C" in FIG. 3 are applicable.

When switch 1 and switch 2 are closed, simulating a grid that is both connected to a grounded object and the molten bath, the responses labeled "G & C" in FIG. 3 are applicable.

FIG. 3 represents results from the test setup described above in which each of the operating conditions were simulated and recorded as events of one minute duration, sampled once per second. Of particular significance is the difference in response between conditions G and G & C. In both instances the measured current escalates from the ground condition as expected; however, the G condition maintains a smooth value because the nature of the ground is such that it is electrically stable so that current travels to ground at a constant value. On the other hand, under the G & C condition the waveform response includes an oscillating component superimposed on the elevated current measurement. Without being held to a particular theory of operation, it is believed that such oscillations result from electrical discontinuities caused by gas bubbles resulting from the injection of feed (e.g. waste) materials into vessel 10 for processing. The importance of this observation is that grid 58 maintains its usefulness as a monitor of the integrity of refractory wall 14 even if grid 58 has previously indicated a false positive ground condition.

Equivalents

Those skilled in the art will recognize, or be able to ascertain using no more than routine experimentation, many equivalents of the invention described specifically herein. Such equivalents are intended to be encompassed in the scope of the following claims.

What is claimed is:

1. An apparatus for monitoring the physical integrity of a vessel comprising:
    a) a vessel having inner and outer walls defining a containment for an electrically-grounded, electrically-conductive liquid;
    b) a detector located within the containment of the vessel;
    c) means for generating an alternating magnetic field in the vicinity of the containment which imposes a corresponding voltage on the detector; and
    d) current sensing means for detecting an induced current flowing through the detector when contacted by the electrically-conductive material, whereby the physical integrity of the containment can be monitored.

2. The apparatus of claim 1 wherein the electrically-conductive liquid comprises a molten bath.

3. The apparatus of claim 2 wherein the molten bath includes a liquid metal.

4. The apparatus of claim 1 wherein the detector is a metal lattice.

5. The apparatus of claim 4 wherein the lattice comprises a stainless steel screen encapsulated in a non-conductive material.

6. The apparatus of claim 5 wherein the non-conductive material is mica.

7. The apparatus of claim 1 wherein the means for generating the alternating magnetic field comprises an induction coil located within the containment and surrounding the detector so as to be transformer coupled thereto.

8. The apparatus of claim 7 wherein the detector is electrically isolated from the induction coil by a high temperature grout and from the electrically-conductive liquid by an inner wall of refractory material.

9. The apparatus of claim 1 wherein the vessel is a molten bath reactor for dissociating waste materials.

10. The apparatus of claim 9 wherein the waste materials are introduced into the molten bath by submerged injection.

11. The apparatus of claim 1 including means coupled to the current sensing means for discriminating between current flow resulting from contact with the electrically-conductive liquid and current flow as the result of contact with other electrically-conductive materials.

12. The apparatus of claim 1 wherein the detector includes a plurality of zones located within the containment of the vessel.

13. An apparatus for monitoring the physical integrity of a vessel comprising:
    a) a vessel having inner and outer walls defining a containment for an electrically-grounded, electrically-conductive liquid;
    b) a detector located within the containment of the vessel;
    c) means for generating an alternating magnetic field in the vicinity of the containment which imposes a corresponding voltage on the detector;
    d) current sensing means for detecting an induced current flowing through the detector when contacted by the electrically-conductive material; and
    e) means coupled to the current sensing means for discriminating between current flow resulting from contact with the electrically-conductive liquid and current flow as the result of contact with other electrically-conductive materials, whereby the physical integrity of the containment can be monitored.

14. The apparatus of claim 13 wherein the electrically-conductive liquid comprises a liquid metal.

15. The apparatus of claim 13 wherein the detector is a metal lattice.

16. The apparatus of claim 15 wherein the lattice comprises a stainless steel screen encapsulated in a non-conductive material.

17. The apparatus of claim 13 wherein the means for generating the alternating magnetic field comprises an induction coil located within the containment and surrounding the detector so as to be transformer coupled thereto.

18. The apparatus of claim 16 wherein the detector is electrically isolated from the induction coil by a high temperature grout and from the electrically-conductive liquid by an inner wall of refractory material.

19. The apparatus of claim 13 wherein the detector includes a plurality of zones located within the containment of the vessel.

20. An apparatus for monitoring the physical integrity of a vessel comprising:
   a) a vessel having inner and outer walls defining a containment for an electrically-grounded, electrically-conductive liquid;
   b) a plurality of detector zones located within the containment of the vessel;
   c) means for generating an alternating magnetic field in the vicinity of the containment which imposes a corresponding voltage on said detector zone; and
   d) current sensing means for detecting an induced current flowing through at least one of the detector zones when contacted by the electrically-conductive material, whereby the physical integrity of the containment can be monitored.

* * * * *